(12) United States Patent
Clark et al.

(10) Patent No.: US 7,799,961 B2
(45) Date of Patent: Sep. 21, 2010

(54) PROCESS OF USING A HIGH ACTIVITY CATALYST FOR THE TRANSALKYLATION OF AROMATICS

(75) Inventors: Michael C. Clark, Chantilly, VA (US); Vijay Nanda, Houston, TX (US); Carlos N. Lopez, Amissville, VA (US); Brian Maerz, Chelmsford, MA (US); Chung-Ming Chi, Needham, MA (US)

(73) Assignees: ExxonMobil Chemical Patents Inc., Houston, TX (US); Stone & Webster, Inc., Houston, TX (US)

( * ) Notice: Subject to any disclaimer, the term of this patent is extended or adjusted under 35 U.S.C. 154(b) by 161 days.

(21) Appl. No.: 11/885,820

(22) PCT Filed: Feb. 24, 2006

(86) PCT No.: PCT/US2006/006539
§ 371 (c)(1),
(2), (4) Date: May 13, 2008

(87) PCT Pub. No.: WO2006/107452
PCT Pub. Date: Oct. 12, 2006

(65) Prior Publication Data
US 2008/0281137 A1 Nov. 13, 2008

Related U.S. Application Data

(60) Provisional application No. 60/666,974, filed on Mar. 31, 2005.

(51) Int. Cl.
*C07C 2/66* (2006.01)
*C07C 6/12* (2006.01)
(52) U.S. Cl. .................. 585/323; 585/467; 585/475
(58) Field of Classification Search ............... 585/323, 585/467, 475
See application file for complete search history.

(56) References Cited

U.S. PATENT DOCUMENTS

| 4,891,458 | A | 1/1990 | Innes et al. |
|---|---|---|---|
| 4,992,606 | A | 2/1991 | Kushnerick et al. |
| 5,334,795 | A | 8/1994 | Chu et al. |
| 5,557,024 | A | 9/1996 | Cheng et al. |
| 2003/0092949 | A1 | 5/2003 | Dandekar et al. |
| 2004/0059167 | A1 | 3/2004 | Clark et al. |

FOREIGN PATENT DOCUMENTS

| EP | 0 719 750 | 7/1996 |
|---|---|---|
| WO | 98/14417 | 4/1998 |
| WO | 2004/056475 | 7/2004 |

*Primary Examiner*—Thuan Dinh Dang
(74) *Attorney, Agent, or Firm*—Darryl M. Tyus; Xiaobing Feng

(57) ABSTRACT

A process for producing an alkylated aromatic compound from polyalkylated aromatic compound(s) having bi-alkylated aromatic compound(s) and tri-alkylated aromatic compound(s), comprising the step of contacting alkylatable aromatic compound(s) with the polyalkylated aromatic compound(s) at a transalkylation condition in the presence of a transalkylation catalyst. The transalkylation catalyst has high activity sufficient to achieve a ratio of bi-alkylated aromatic compound(s) conversion over tri-alkylated aromatic compound(s) conversion in a range of from about 0.5 to about 2.5.

8 Claims, No Drawings

PROCESS OF USING A HIGH ACTIVITY CATALYST FOR THE TRANSALKYLATION OF AROMATICS

CROSS REFERENCE TO RELATED APPLICATIONS

This application is a 35 U.S.C. 371 National Stage Application of International Application No. PCT/US2006/006539, filed Feb. 24, 2006, which claims the benefit of Provisional Application No. 60/666,974, filed Mar. 31, 2005, the disclosures of which are hereby incorporated by reference in their entireties.

BACKGROUND OF THE INVENTION

The present invention relates to a process for the transalkylation of aromatics, particularly the transalkylation of polyisopropylbenzene (PIPB) with benzene to produce cumene and the transalkylation of polyethylbenzene (PEB) with benzene to produce ethylbenzene. Ethylbenzene is a valuable commodity chemical and is used in the production of styrene monomer. Cumene (isopropylbenzene) is also a valuable commodity chemical and is used in the production of phenol and acetone.

Presently, ethylbenzene is often produced by a liquid phase alkylation process from benzene and ethylene in the presence of an alkylation catalyst. The liquid phase process operates at a lower temperature than its vapor phase counterpart. One advantage of the liquid phase alkylation is a lower yield of undesired by-products, polyalkylated aromatic compound(s). The alkylation of aromatic hydrocarbon compounds employing zeolite catalysts is known and understood in the art. U.S. Pat. No. 5,334,795 describes the liquid phase alkylation of benzene with ethylene in the presence of MCM-22 to produce ethylbenzene; and U.S. Pat. No. 4,891,458 discloses liquid phase alkylation and transalkylation processes using zeolite beta.

Zeolite-based catalysts are used in the alkylation of benzene with propylene to produce cumene. U.S. Pat. No. 4,992,606 discloses a process for preparing cumene using MCM-22 in liquid phase.

Commercial alkylation processes for the production of ethylbenzene and cumene typically produce certain polyalkylated by-products in addition to ethylbenzene and cumene. The polyalkylated aromatic compound(s) may be transalkylated with benzene or other alkylatable aromatic compound(s) to produce ethylbenzene or cumene. This transalkylation reaction may be accomplished by feeding the polyalkylated aromatic compound(s) through a transalkylation reactor operated under suitable conditions and in the presence of a transalkylation catalyst. Also, the polyalkylated aromatic compound(s) may be recycled to an alkylation reactor in the presence of an alkylation catalyst that is capable of performing the transalkylation reaction. The polyalkylated aromatic compound(s) typically include bi-alkylated benzenes (e.g., bi-ethylbenzene(s) or bi-isopropylbenzenes) and tri-alkylated benzene(s) (e.g., tri-ethylbenzenes or tri-isopropylbenzenes). Commercial transalkylation catalysts typically have bi-alkylated benzenes conversion of about 50 wt. % to 90 wt. %, but low tri-alkylated benzenes conversion (e.g., less than 20 wt. %) under the same conditions. U.S. Pat. No. 5,557,024 discloses a process for preparing short chain alkyl aromatic compounds using MCM-56 and the use of zeolite catalysts such as MCM-22, zeolite X, zeolite Y and zeolite beta for the transalkylation of the polyalkylated aromatic compound(s).

However, none of these references contemplate a transalkylation process with a transalkylation catalyst which is maintained under conditions sufficient to yield a ratio of bi-alkylated aromatic compound(s) conversion over tri-alkylated aromatic compound(s) conversion in a range of from about 0.5 to about 2.5 at a temperature less than 300° C.

SUMMARY OF THE INVENTION

In one embodiment, this invention relates to a process for producing an alkylated aromatic compound from polyalkylated aromatic compound(s) having bi-alkylated aromatic compound(s) and tri-alkylated aromatic compound(s), comprising the step of contacting alkylatable aromatic compound(s) with the polyalkylated aromatic compound(s) at a transalkylation condition in the presence of a transalkylation catalyst, wherein the transalkylation catalyst is maintained under conditions sufficient to yield a ratio of bi-alkylated aromatic compound(s) conversion over tri-alkylated aromatic compound(s) conversion in a range of from about 0.5 to about 2.5, preferably, about 0.5 to about 1.5, even more preferably, about 0.5 to about 1, still more preferably about 0.75 to about 1.25, and most preferably, about 0.9 to about 1.2. In another embodiment, the alkylated aromatic compound is cumene, wherein the ratio of bi-alkylated aromatic compound(s) conversion over tri-alkylated aromatic compound(s) conversion in a range of from about 0.5 to about 1, preferably, about 0.5 to 0.9, and most preferably, about 0.6 to about 0.9.

In another embodiment, this invention relates to a process for producing an alkylated aromatic compound, comprising the steps of:

contacting an alkylatable aromatic compound with an alkylating agent under alkylation conditions in the presence of an alkylation catalyst, to produce an alkylation effluent having an alkylated aromatic compound and polyalkylated aromatic compound(s) including bi-alkylated aromatic compound(s) and tri-alkylated aromatic compound(s); and contacting the polyalkylated aromatic compound(s) with a feedstock having the alkylatable aromatic compound in the presence of a transalkylation catalyst to provide a transalkylation effluent which comprises additional alkylated aromatic compound, wherein the transalkylation catalyst is maintained under conditions sufficient to yield a ratio of a bi-alkylated aromatic compound(s) conversion over a tri-alkylated aromatic compound(s) conversion in a range of from about 0.5 to about 2.5.

In one aspect of any of the above embodiments, the transalkylation catalyst comprises at least one of MCM-22, MCM-36, MCM-49, MCM-56, zeolite beta, faujasite, mordenite, PSH-3, SSZ-25, ERB-1, ITQ-1, ITQ-2, zeolite Y, Ultrastable Y (USY), Dealuminized Y, rare earth exchanged Y (REY), ZSM-3, ZSM-4, ZSM-18, ZSM-20, and any combination thereof.

In a preferred embodiment of this invention, the transalkylation catalyst is zeolite Y. In another preferred embodiment of this invention, the transalkylation is a zeolite having a zeolite type of FAU.

In one embodiment, the alkylated compound is cumene, the alkylatable aromatic compound(s) includes benzene, and the polyalkylated compound(s) include polyisopropylbenzene(s). In another embodiment, the alkylated aromatic compound is ethylbenzene, the alkylatable aromatic compound(s) includes benzene, and the polyalkylated aromatic compound(s) includes polyethylbenzene(s).

In one aspect of any of above embodiment, the transalkylation conditions include a temperature of 150 to 260° C. and a pressure of 696 to 4137 kPa-a (101 to 600 psia), a WHSV based on the weight of the polyalkylated aromatic compounds of about 0.5 to 100 hr$^{-1}$, a mole ratio of the alkylatable aromatic compound to the polyalkylated aromatic compounds of 1:1 to 10:1.

In another aspect of any of above embodiment, the bi-alkylated aromatic compound(s) conversion is in the range of about 25 wt. % to about 95 wt. %. In yet another aspect of any of above embodiment, the bi-alkylated aromatic compound(s) conversion is in the range of about 45 wt. % to about 75 wt. %.

In one aspect of any of the above embodiment, the alkylation catalyst comprises at least one of MCM-22, MCM-36, MCM-49, MCM-56, and any combination thereof.

In one preferred embodiment, the alkylated aromatic compound is ethylbenzene, the alkylatable aromatic compound comprises benzene, the alkylating agent comprises at least 10 mol. % ethylene, the polyalkylated aromatic compound(s) comprise polyethylbenzenes(s). In another preferred embodiment, the alkylated aromatic compound is cumene, the alkylatable aromatic compound comprises benzene, the alkylating agent comprises propylene, and the polyalkylated aromatic compound(s) comprise polyisopropylbenzenes(s).

In one embodiment of this invention, the alkylating agent comprises at least one of a concentrated alkene feedstock, a dilute alkene feedstock, or any combination thereof.

In another embodiment, this invention relates to a method for retrofitting an existing an ethylbenzene or cumene plant(s) to produce ethylbenzene or cumene.

In another embodiment, this invention relates to a method for retrofitting an existing an ethylbenzene or cumene plant(s) having a heat integration between an alkylation reactor and a transalkylation reactor to produce ethylbenzene or cumene. In another embodiment, this invention relates to a method for retrofitting an existing an ethylbenzene or cumene plant(s) having a de-coupled heat integration between an alkylation reactor and a transalkylation reactor to produce ethylbenzene or cumene.

In one embodiment, this invention relates to a method for selecting an alkylation catalyst for a process have an alkylation step and a transalkylation step, the method comprising the steps of:
(a) selecting a transalkylation catalyst having at least one of zeolite having a zeolite structure type of FAU, *BEA, MWW, MTW, and any combination thereof, wherein the transalkylation is maintained under conditions including temperature and pressure to ensure to yield a ratio of a bi-alkylated aromatic compound(s) conversion over a tri-alkylated aromatic compound(s) conversion in a range of from about 0.5 to about 2.5; and
(b) selecting an alkylation catalyst having at least one of MCM-22, MCM-36, MCM-49, MCM-56, and any combination thereof, wherein the alkylation catalyst is sufficiently active to maintain at least 90 mol. % alkene conversion at a temperature range from about 50° C. below the temperature of step (a) to about 100° C. above the temperature of step (a).

In yet another embodiment, this invention relates to a method for selecting a transalkylation catalyst for a process have an alkylation step and a transalkylation step, the method comprising the steps of:
(a) selecting an alkylation catalyst having at least one of MCM-22, MCM-36, MCM-49, MCM-56, and any combination thereof, wherein the alkylation catalyst is maintained under conditions including temperature and pressure to ensure at least 90 mol. % alkene conversion; and
(b) selecting a transalkylation catalyst having at least one of zeolite having a zeolite structure type of FAU, *BEA, MWW, MTW, and any combination thereof, wherein the transalkylation is sufficiently active to yield a ratio of a bi-alkylated aromatic compound(s) conversion over a tri-alkylated aromatic compound(s) conversion in a range of from about 0.5 to about 2.5 in a temperature range from about 100° C. below the temperature of step (a) to about 50° C. above the temperature of step (a).

In one aspect of any above embodiments, the transalkylation catalyst is maintained under conditions sufficient to yield a ratio of bi-alkylated aromatic compound(s) rate-constant over tri-alkylated aromatic compound(s) rate-constant in a range of from about 0.5 to about 4.

DETAILED DESCRIPTION OF THE INVENTION

The present invention relates to a process of using that exhibits unexpectedly higher relative catalytic activity as compared to conventional transalkylation catalyst. The catalyst comprises at least one of MCM-22, MCM-36, MCM-49, MCM-56, zeolite beta, faujasite, mordenite, PSH-3, SSZ-25, ERB-1, ITQ-1, ITQ-2, zeolite Y, Ultrastable Y (USY), Dealuminized Y, rare earth exchanged Y (REY), ZSM-3, ZSM-4, ZSM-18, ZSM-20, and any combination thereof. The transalkylation catalyst is maintained under conditions sufficient to yield a ratio of bi-alkylated aromatic compound(s) conversion over tri-alkylated aromatic compound(s) conversion in a range of from about 0.5 to about 2.5, preferably, about 0.5 to about 1.5, even more preferably, about 0.5 to about 1, still more preferably about 0.75 to about 1.25, and most preferably, about 0.9 to about 1.2. In another embodiment, the alkylated aromatic compound is cumene, wherein the ratio of bi-alkylated aromatic compound(s) conversion over tri-alkylated aromatic compound(s) conversion in a range of from about 0.5 to about 1, preferably, about 0.5 to 0.9, and most preferably, about 0.6 to about 0.9.

A molecular sieve typically contains at least two elements selected from the group consisting of Si, Al, P, Ge, Ga and Ti, most particularly selected from Si, Al and Ti. Exemplary molecular sieves useful for transalkylation have the structure types FAU, *BEA, MTW, MWW, and any combination thereof. See "Atlas of Zeolite Structure Types", W. H. Meier, D. H. Olson, C. H. Baerlocher, Elsevier, 4th Edition, 1996, the disclosure of which is incorporated herein by reference. Particularly suitable molecular sieves include zeolite beta, zeolite Y, MCM-22, and ZSM-12.

The invention also relates to a process for producing a monoalkylated aromatic compound wherein an alkylation step, carried out under at least partial liquid phase conditions, an alkylatable compound is reacted with an alkylating agent, to produce a monoalkylated aromatic end product as well as a polyalkylated compound, which is separated and fed to a transalkylation process step. In the transalkylation step, which is also preferably conducted under at least partial liquid phase conditions, the polyalkylated end product is contacted in a transalkylation reactor with an alkylatable aromatic compound in the presence of a transalkylation catalyst to produce a monoalkylated compound. The alkylation and the transalkylation catalysts comprise at least one of MCM-22, MCM-36, MCM-49, MCM-56, zeolite beta, faujasite, mordenite, PSH-3, SSZ-25, ERB-1, ITQ-1, ITQ-2, zeolite Y, Ultrastable Y (USY), Dealuminized Y, rare earth exchanged Y (REY), ZSM-3, ZSM-4, ZSM-18, ZSM-20, and any combination thereof.

The term "aromatic" when used in reference to the alkylatable compounds which are useful herein is to be understood in accordance with its art-recognized scope which includes alkyl-substituted and unsubstituted mono- and polynuclear compounds. Compounds of an aromatic character that possess a heteroatom are also useful provided they do not act as catalyst poisons under the reaction conditions selected.

Substituted aromatic compounds that may be alkylated in accordance with the present invention, such as alkylatable aromatic compounds, must possess at least one hydrogen atom directly bonded to the aromatic nucleus. The aromatic rings can be substituted with one or more alkyl, aryl, alkylaryl, alkoxy, aryloxy, cycloalkyl, halide, and/or other groups that do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds, such as alkylating agents, include toluene, xylene, isopropylbenzene, normal propylbenzene (n-propylbenzene), alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene, 1,2,4-triethylbenzne; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenathrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate containing substantial quantities of benzene, toluene and/or xylene constitutes a particularly useful feed for the alkylation process of this invention.

The alkylating agents that may be useful in the process of this invention generally include any aliphatic or aromatic organic compounds having one or more available alkylating aliphatic groups capable of reaction with the alkylatable aromatic compound.

Preferably, the alkylating agent employed herein has at least one alkylating aliphatic group possessing from 1 to 5 carbon atoms. Examples of such alkylating agents are olefins such as ethylene, propylene, the butenes, and the pentenes; alcohols (inclusive of monoalcohols, dialcohols and trialcohols) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides and the pentyl chlorides.

Mixtures of light olefins are especially useful as alkylating agents in the alkylation process of this invention. A mixture of concentrate alkene stream having at least 80 mol. % alkene and a dilute alkene stream having about 10 mol. % to 80 mil. % alkene may be used for this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins and refinery FCC propane/propylene streams, are useful are useful alkylating agents herein. For example, a typical FCC light olefin stream possesses the following composition:

|  | Wt. % | Mole % |
| --- | --- | --- |
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products which may be obtained from the process of the invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes. Preferably, the process of the invention relates to the production of ethylbenzene by the alkylation of benzene with ethylene followed by the transalkylation of the diethylbenezene by-products with additional benzene; the production of cumene by the alkylation of benzene with propylene followed by the transalkylation of the diisopropylbenzene by-products with additional benzene.

In one embodiment of the invention, the alkylation process of this invention is conducted such that the organic reactants, i.e., the alkylatable aromatic compound and the alkylating agent, are brought into contact with an alkylation or transalkylation catalyst in a suitable alkylation or transalkylation reaction zone such as, for example, in a flow reactor containing a fixed bed of the catalyst composition, under effective alkylation conditions. Such conditions include a temperature of from about 0° C. to about 500° C. (32° F. to 932° F.), and preferably between about 50° C. and about 300° C. (122° F. to about 572° F.), more preferably, between about 100 to about 285° C. (212 to 545° F.), a pressure of 689 to 4601 kpa-a (100 to 667 psia), preferably, a pressure of 1500 to 3500 kPa-a (218 to 508 psia), a WHSV based on alkene for overall reactor of 0.1 to 10 $hr^{-1}$, preferably, 0.2 to 2 $hr^{-1}$, more preferably, 0.5 to 1 $hr^{-1}$, or a WHSV based on both alkene and benzene for overall reactor of 10 to 100 $hr^{-1}$, preferably, 20 to 50 $hr^{-1}$, a molar ratio of alkylatable aromatic compound to alkylating agent of from about 0.1:1 to about 50:1, and preferably can be from about 0.5:1 to about 10:1.

The reactants can be in either the vapor phase or partially or completely in the liquid phase and can be neat, i.e., free from intentional admixture or dilution with other material, or they can be brought into contact with the zeolite catalyst composition with the aid of carrier gases or diluents such as, for example, hydrogen and nitrogen.

In another embodiment of the invention, when benzene is alkylated with ethylene to produce an alkylation reactor effluent that contains ethylbenzene. The alkylation reaction is preferably carried out in the liquid phase under conditions including a temperature between 300° F. and 600° F. (about 150° C. to 316° C.), more preferably between 400° F. and 500° F. (about 205° C. and 260° C.), a pressure up to about 3000 psig (20865 kPa), more preferably between 400 and 800 psig (2869 and 5600 kPa), a weight hourly space velocity (WHSV) between about 0.1 and 20 hr$^{-1}$, more preferably between 0.5 hr$^{-1}$ and 6 hr$^{-1}$, based on the ethylene feed, and a ratio of the benzene to the ethylene in the alkylation reactor from 1:1 to 30:1 molar, more preferably from about 1:1 to 10:1 molar.

In still another embodiment of the invention, when benzene is alkylated with propylene to produce an alkylation reactor effluent that contains cumene. The alkylation reaction may also take place under liquid phase conditions including a temperature of up to about 482° F. (250° C.), e.g., up to about 302° F. (150° C.), e.g., from about 50° F. to about 257° F. (10° C. to 125° C.); a pressure of about 250 atmospheres (25,000 kPa) or less, e.g., from about 1 to about 30 atmospheres (100 kPa-3000 kPa); and an aromatic hydrocarbon weight hourly space velocity 5 hr$^{-1}$ to about 250 hr$^{-1}$, preferably from 5 hr$^{-1}$ to 50 hr$^{-1}$.

The alkylation or transalkylation catalyst that may be useful in this invention is a crystalline molecular sieve preferably selected from MCM-22 (described in detail in U.S. Pat. No. 4,954,325), MCM-36 (described in detail in U.S. Pat. No. 5,250,277), MCM-49 (described in detail in U.S. Pat. No. 5,236,575), MCM-56 (described in U.S. Pat. No. 5,362,697), and zeolite beta (described in detail in U.S. Pat. No. 3,308,069).

One embodiment of this invention is a method of selecting a transalkylation catalyst based on the selection of the alkylation catalyst or verse visa. By selecting one catalyst of these two interrelated reactions (alkylation and transalkylation), the preferred reaction conditions and corresponding product composition are determined. Based on the selection of one of these two reactions, the selection of the catalyst for another reaction can be determined based on the results to be achieved.

In one embodiment, this invention relates to a method for selecting an alkylation catalyst for a process have an alkylation step and a transalkylation step, the method comprising the steps of:

(a) selecting a transalkylation catalyst having at least one of zeolite having a zeolite structure type of FAU, *BEA, MWW, MTW, and any combination thereof, wherein the transalkylation is maintained under conditions including temperature and pressure to ensure to yield a ratio of a bi-alkylated aromatic compound(s) conversion over a tri-alkylated aromatic compound(s) conversion in a range of from about 0.5 to about 2.5; and (b) selecting an alkylation catalyst having at least one of MCM-22, MCM-36, MCM-49, MCM-56, and any combination thereof, wherein the alkylation catalyst is sufficiently active to maintain at least 90 mol. %, preferably 95 mol. %, even more preferably, 99 mol. %, alkene conversion at a temperature range from about 50° C. below the temperature of step (a) to about 100° C. above the temperature of step (a).

In yet another embodiment, this invention relates to a method for selecting a transalkylation catalyst for a process have an alkylation step and a transalkylation step, the method comprising the steps of:

(a) selecting an alkylation catalyst having at least one of MCM-22, MCM-36, MCM-49, MCM-56, and any combination thereof, wherein the alkylation catalyst is maintained under conditions including temperature and pressure to ensure at least 90 mol. %, preferably 95 mol. %, even more preferably, 99 mol. %, alkene conversion; and (b) selecting a transalkylation catalyst having at least one of zeolite having a zeolite structure type of FAU, *BEA, MWW, MTW, and any combination thereof, wherein the transalkylation is sufficiently active to yield a ratio of a bi-alkylated aromatic compound(s) conversion over a tri-alkylated aromatic compound(s) conversion in a range of from about 0.5 to about 2.5 in a temperature range from about 100° C. below the temperature of step (a) to about 50° C. above the temperature of step (a).

The alkylation reactor effluent contains the excess aromatic feed, monoalkylated aromatic compounds (such as ethylbenzene or cumene), polyalkylated aromatic compounds (such as polyethylbenzene or polyisopropylbenzene), and various impurities. The aromatic feed is recovered by distillation and recycled to the alkylation reactor. Usually a small bleed is taken from the recycle stream to eliminate unreactive impurities from the loop. The bottoms from the benzene distillation are further distilled to separate monoalkylated product from polyalkylated products and other heavies.

The term "polyethylbenzene" (PEB) in reference to the polyalkylated aromatic compounds which are useful herein is to be understood in accordance with its art-recognized scope which includes, by way of illustration and not limitation, diethylbenzene (DEB) and triethylbenzene (TEB).

The term "polyisopropylbenzene" (PIPB) in reference to polyalkylated aromatic compounds which are useful herein is to be understood in accordance with its art-recognized scope which includes, by way of illustration and not limitation, diisopropylbenzene (DIPB) and triisopropylbenzene (TIPB).

The polyalkylated products separated from the alkylation reactor effluent are reacted with alkylatable aromatic feed in a transalkylation reactor, which may or may not be separated from the alkylation reactor, over a suitable transalkylation catalyst. According to the invention, the transalkylation catalyst comprises at least one of MCM-22, MCM-36, MCM-49, MCM-56, zeolite beta, faujasite, mordenite, PSH-3, SSZ-25, ERB-1, ITQ-1, ITQ-2, zeolite Y, Ultrastable Y (USY), Dealuminized Y, rare earth exchanged Y (REY), ZSM-3, ZSM-4, ZSM-18, ZSM-20, and any combination thereof.

The transalkylation reaction of the invention is conducted under at least partial liquid phase conditions such that the polyalkylated aromatics react with additional alkylatable aromatic compounds to produce additional monoalkylated product. Suitable transalkylation conditions include a temperature of 100° C. to 260° C. (212° F. to 500° F.), a pressure of 696 to 5100 kpa-a (101-740 psia), a WHSV based on the weight of the polyalkylated aromatic compounds of about 0.5 to 200 hr$^{-1}$, and alkylatable aromatic compounds/polyalkylated benzene weight ratio 0.5:1 to 20:1. Preferably, a temperature of 150 to 260° C. and a pressure of 696 to 4137 kPa-a (101 to 600 psia), a WHSV based on the weight of the polyalkylated aromatic compounds of about 0.5 to 100 hr$^{-1}$, a mole ratio of the alkylatable aromatic compound to the polyalkylated aromatic compounds of 1:1 to 10:1

In one embodiment of this invention, there is a heat integration between the alkylation reactor and the transalkylation reactor. For example, the effluent from the alkylation reactor may be used to heat the feed stream of the transalkylation reactor. The effluent from the alkylation reactor may be used to generate steam. In another embodiment of this invention, the heat integration between the alkylation reactor and the transalkylation reactor can be de-coupled. The advantage of de-coupling the heat integration between the alkylation reactor and the transalkylation reactor is that the conditions of the alkylation reactor can be independent determined to the conditions of the transalkylation reactor. Therefore, it is possible to achieve optimum results of these two reactions independently.

Reaction rate-constants were calculated using methods known to those skilled in the art. See "Principles and Practice of Heterogeneous Catalyst", J. M. Thomas, W. J. Thomas, VCH, $1^{st}$ Edition, 1997, the disclosure of which is incorporated herein by reference. Reaction rate constants were calculated for both DEB and TEB under reaction conditions (temperature, pressure, and WHSV) and the ratio of these reaction rate constants was then calculated to examine the relative rates of DEB and TEB conversion. The reactions were assumed to be first order with respect to DEB and TEB and zero order with respect to benzene since it is in excess.

In another embodiment of this invention, the process of this invention can be used to retrofit existing ethylbenzene or cumene plant. In yet another embodiment of this invention, the process of this invention can be used to retrofit existing $AlCl_3$ or $BF_3$ plant. The retrofitting can be done by replacing existing processes and catalysts with the processes and catalysts of this invention. The advantage of retrofitting existing plants is low cost.

In one embodiment of this invention, the transalkylation catalyst is maintained under conditions sufficient to yield a ratio of bi-alkylated aromatic compound(s) rate-constant over tri-alkylated aromatic compound(s) rate-constant in a range of from about 0.5 to about 4, preferably, about 0.5 to 1.5, even more preferably, about 0.5 to about 1, still more preferably about 0.75 to about 1.25, and most preferably, about 0.9 to about 1.2. In another embodiment, the alkylated aromatic compound is cumene, wherein the ratio of bi-alkylated aromatic compound(s) conversion over tri-alkylated aromatic compound(s) conversion in a range of from about 0.5 to about 1, preferably, about 0.5 to 0.9, and most preferably, about 0.6 to about 0.9.

When the polyalkylated aromatics are polyisopropylbenzenes and are contacted with benzene to produce cumene in a transalkylation reactor, the transalkylation conditions preferably include a temperature 50° F. to about 100° F. (100° C. to 200° C.), a pressure of 20 to 30 barg (2100-3100 kPa), weight hourly space velocity of 10 to 72 $hr^{-1}$ on total feed and benzene/PIPB weight ratio 1:1 to 6:1.

When the polyalkylated aromatics are polyethylbenzenes and are contacted with benzene to produce ethylbenzene in a transalkylation reactor, the transalkylation conditions preferably include a temperature of 428° F. to about 500° F. (220 to 260° C.), a pressure of 20 to 30 barg (2100-3100 kPa-a), weight hourly space velocity of 2 to 6 $hr^{-1}$ on total feed and benzene/PEB weight ratio 2:1 to 6:1.

The effluent from the transalkylation reactor is blended with alkylation reactor effluent and the combined stream distilled to separate the desired monoalkylated product.

The present invention will be described in the following examples.

EXAMPLE

Transalkylation of PEB to EB

The transalkylation feed used in Example was prepared as follows. Chemical grade benzene and para- and meta-diethylbenzene were purified by percolation over activated alumina. The purified diethylbenzene were mixed 2:1 by weight (para:meta). The purified benzene and polyethylbenzenes were mixed 2:1 weight ratio and stored under nitrogen. A gas chromatograph (GC) analysis of the feed provided the composition by weight shown in Table I.

Two catalysts were tested for transalkylation reaction, a conventional commercial transalkylation catalyst (low activity catalyst) is made using a zeolite with a structure type of MOR, a $Si/Al_2$ of about 35, a surface area of about 390 $m^2/g$, and extruded to form 1/16" diameter cylindrical extrudates with 20 wt. % alumina. A high activity transalkylation catalyst is made with a zeolite with a structure type of FAU, a $Si/Al_2$ ratio of about 30, a surface area of about 780 $m^2/g$ and extruded to form 1/16" diameter cylindrical extrudates with 20 wt. % alumina.

Liquid feed, which has a composition as shown in table 1, was introduced with calibrated diaphragm pump. A 12.7 mm (½") pipe was used for the reaction vessels and contained 30-35 g of catalyst operated in a downflow configuration in isothermal mode. The operating pressure for all experiments was 3204 KPa-a (465 psia). Temperature, Weight Hourly Space Velocity (WHSV) and Benzene:Polyethylbenzene (B:PEB) ratio are indicated in the table along with the corresponding Diethylbenzene (DEB) and triethylbenzene (TEB) conversion and their corresponding first order rate constants (k). The total product was chilled and analyzed with an off-line gas chromatograph equipped with a flame ionization detector. Results are shown in Table 2.

TABLE 1

| Component | Composition (wt. %) |
| --- | --- |
| Benzene | 60.0 |
| Ethylbenzene | 0.1 |
| m-diethylbenzene (m-DEB) | 19.1 |
| p-diethylbenzene (p-DEB) | 9.3 |
| o-diethylbenzene (o-DEB) | 7.7 |
| 1,3,5-triethylebnzene (135-TEB) | 1.8 |
| 1,2,4-triethylebnzene (124-TEB) | 1.8 |
| 1,2,3-triethylebnzene (123-TEB) | 0.1 |

TABLE 2

| | Low Activity Catalyst | High Activity Catalyst | High Activity Catalyst | High Activity Catalyst |
| --- | --- | --- | --- | --- |
| T (° C.) | 240 | 200 | 207 | 200 |
| B:PEB (mol:mol) | 1.8 | 1.4 | 1.4 | 1.5 |
| WHSV ($hr^{-1}$) | 1.4 | 1.5 | 1.5 | 1.3 |
| DEB rate-constant ($hr^{-1}$) | 0.9 | 1.2 | 1.4 | 1.5 |
| TEB rate-constant ($hr^{-1}$) | 0.2 | 1.0 | 1.6 | 1.7 |
| DEB Conversion (wt. %) | 48% | 59% | 63% | 65% |
| TEB Conversion (wt. %) | 16% | 50% | 67% | 70% |
| Heavies yield (wt. %) | 1.8% | 0.6% | 0.7% | 0.6% |

The high activity transalkylation catalyst of this invention has a surprisingly low ratio of DEB conversion over TEB conversion which is in the range of 0.9 to 1.18, in comparison with conventional transalkylation catalyst having a ratio of DEB conversion over TEB conversion of 3.

The high activity transalkylation catalyst of this invention has a surprisingly low ratio of DEB rate-constant over TEB rate-constant which is in the range of 0.875 to 1.2, in comparison with conventional transalkylation catalyst having a ratio of DEB rate-constant over TEB rate-constant of 4.5.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A process for producing ethylbenzene comprising the steps of:
   (a) selecting an alkylation catalyst which comprises at least one zeolite selected from the group consisting of MCM-22, MCM-36, MCM-49, MCM-56, and any combination thereof;
   (b) contacting an alkylatable aromatic compound(s) which comprises benzene, with an alkylating agent under alkylation conditions in the presence of said alkylation catalyst in an alkylation reactor, to produce an alkylation effluent which comprises polyalkylated aromatic compound(s) which comprises bi-alkylated aromatic compound(s) and tri-alkylated aromatic compound(s), said bi-alkylated aromatic compound(s) comprises diethylbenzene, said tri-alkylated compound(s) comprises triethylbenzene;
   (c) selecting a transalkylation catalyst which comprises at least one zeolite having a zeolite structure type of FAU;
   (d) contacting said alkylatable aromatic compounds with polyalkylated aromatic compound(s) at transalkylation conditions in the presence of said transalkylation catalyst in a transalkylation reactor to produce a transalkylation effluent comprising said ethylbenzene,
   wherein the selected alkylation catalyst is maintained under alkylation conditions of temperature and pressure to ensure at least 90 mol. % alkene conversion;
   wherein said transalkylation conditions comprises a temperature range from about 100° C. below the temperature of step (b) to about 50° C. above the temperature of step (b) to yield a ratio of a bi-alkylated aromatic compound(s) conversion over a tri-alkylated aromatic compound(s) conversion in a range of from about 0.9 to 1.18;
   wherein said alkylation effluent is used to heat said alkylatable aromatic compound, said polyalkylated aromatic compound(s) or steam.

2. The process claim 1, wherein said transalkylation conditions include a temperature of 150 to 260° C. and a pressure of 696 to 4137 kPa-a (101 to 600 psia), a WHSV based on the weight of said polyalkylated aromatic compounds of 0.5 to 100 hr$^{-1}$, a mole ratio of said alkylatable aromatic compound to said polyalkylated aromatic compounds of 1:1 to 10:1.

3. The process of claim 1, wherein the conversion of diethylbenzene is in the range of 25 wt. % to 95 wt. %.

4. The process of claim 1, wherein the conversion of diethylbenzene is in the range of 45 wt. % to 75 wt. %.

5. The process of claim 1, further comprising the step of separating said alkylation effluent to recover said polyalkylated aromatic compound(s).

6. The process of claim 1, further comprising the step of separating said alkylation effluent or said transalkylation effluent, to recover said ethylbenzene.

7. The process of claim 1, wherein said alkylating agent comprises ethylene feedstock.

8. The process of claim 7, wherein said alkylating agent comprises at least one of a concentrated ethylene feedstock, a dilute ethylene feedstock of at least 10 mol. % ethylene, or any combination thereof.

* * * * *